(12) United States Patent
Menn et al.

(10) Patent No.: US 9,709,384 B2
(45) Date of Patent: Jul. 18, 2017

(54) DEVICE FOR MONITORING FOULING DEPOSITS IN A PULVERIZED COAL FURNACE

(71) Applicants: Anatoly Naftaly Menn, Haifa (IL); Joseph Krimerman, Haifa (IL)

(72) Inventors: Anatoly Naftaly Menn, Haifa (IL); Joseph Krimerman, Haifa (IL)

(73) Assignee: AB Sensing, Inc., Newton Centre, MA (US)

( * ) Notice: Subject to any disclaimer, the term of this patent is extended or adjusted under 35 U.S.C. 154(b) by 13 days.

(21) Appl. No.: 14/440,770

(22) PCT Filed: Jun. 28, 2013

(86) PCT No.: PCT/IB2013/002336
§ 371 (c)(1),
(2) Date: May 5, 2015

(87) PCT Pub. No.: WO2014/072780
PCT Pub. Date: May 15, 2014

(65) Prior Publication Data
US 2015/0285620 A1 Oct. 8, 2015

Related U.S. Application Data

(60) Provisional application No. 61/796,351, filed on Nov. 8, 2012.

(51) Int. Cl.
F22B 37/54 (2006.01)
F22B 37/00 (2006.01)
(Continued)

(52) U.S. Cl.
CPC .......... *G01B 11/0625* (2013.01); *F22B 37/54* (2013.01); *G01N 21/55* (2013.01); *F22B 37/003* (2013.01); *F27D 21/0021* (2013.01)

(58) Field of Classification Search
CPC ........ F22B 37/003; F22B 37/54; F27D 21/02; F27D 21/0021; G01J 3/06; G01J 11/0625
(Continued)

(56) References Cited

U.S. PATENT DOCUMENTS

| 4,466,383 A * | 8/1984 | Klatt ...................... F22B 37/56 |
| | | 122/379 |
| 4,514,096 A | 4/1985 | Wynnyckyj et al. |

(Continued)

FOREIGN PATENT DOCUMENTS

| CN | 100430703 C | 11/2008 |
| DE | 44 25 187 A1 | 1/1996 |

OTHER PUBLICATIONS

"Specifications of the Infra-View Infrared Sensor", retrieved online on Feb. 11, 2004 at www.infra-view.com/infrared_sensor.htm.
(Continued)

*Primary Examiner* — Gregory A Wilson
(74) *Attorney, Agent, or Firm* — Posternak Blankstein & Lund LLP

(57) ABSTRACT

A method of direct on-line measurement of thickness of fouling deposits created on the tube walls in a pulverized-coal firing furnace is described, as well as an apparatus suitable for implementation of the method. The method is based on imaging of a light spot, generated on the deposit surface by the apparatus. A position-sensitive image detector is used to track the spot as deposits accumulate, and the image signal is processed in real time, which allows for monitoring the creation of fouling deposits during operation of the furnace. The system simultaneously determines the reflectivity of the deposit surface. The apparatus can be used as part of an automatic soot blowing system.

43 Claims, 5 Drawing Sheets

(51) Int. Cl.
*G01B 11/06* (2006.01)
*G01N 21/55* (2014.01)
*F27D 21/00* (2006.01)

(58) Field of Classification Search
USPC .......................... 122/379, 396; 239/750, 752
See application file for complete search history.

(56) References Cited

U.S. PATENT DOCUMENTS

| | | | |
|---|---|---|---|
| 6,485,174 B1 | 11/2002 | Albrecht et al. | |
| 8,418,662 B2* | 4/2013 | Kim | F22B 37/003 |
| | | | 122/363 |
| 9,207,211 B2* | 12/2015 | Kawata | F22B 37/003 |
| 9,360,207 B2* | 6/2016 | Debroise | F22B 37/003 |
| 2004/0032583 A1 | 2/2004 | Huston et al. | |
| 2005/0235927 A1* | 10/2005 | Hwang | F22B 37/003 |
| | | | 122/379 |
| 2008/0084565 A1 | 4/2008 | Zribi et al. | |
| 2008/0317447 A1* | 12/2008 | Lentz | F22B 1/284 |
| | | | 392/326 |
| 2012/0270162 A1 | 10/2012 | Dahlhielm et al. | |
| 2016/0025600 A1* | 1/2016 | Carlier | F28G 15/02 |
| | | | 73/788 |
| 2016/0201896 A1* | 7/2016 | Hicks | F22B 37/486 |
| | | | 122/379 |

OTHER PUBLICATIONS

R. Korbee, et al., "Monitoring and Modelling of Gas-Side Boiler Fouling", ECI Symposium Series, vol. RP2: Proceedings of the 6th International Conference on Heat Exchanger Fouling and Cleaning—Challenges and Opportunuites, Germany, Jun. 5-10, 2005, pp. 248-254.

S. Krüger, et al., "Characterisation of Deposits on Membrane Walls of Steam Generators by Heat Flux Density Measurement", Proceedings of the International Conference on Incineration and Thermal Treatment Technologies—IT3, Montreal, Quebec, Canada, May 12-16, 2008, 12 pgs.

* cited by examiner

DEVICE FOR MONITORING FOULING DEPOSITS IN A PULVERIZED COAL FURNACE

CROSS REFERENCE TO RELATED APPLICATIONS

This application claims the priority of U.S. Provisional Application No. 61/796,351 filed Nov. 8, 2012 and entitled "Arrangement for Measuring Reflectivity/Emissivity of Fouling Deposits in a Pulverized Coal Firing Furnace", the whole of which is hereby incorporated by reference.

BACKGROUND

It is well known that the problem of fouling exists while burning solid fuels, such as pulverized coal, in industrial furnaces used in power stations. Contaminants deposited on the water tubes inside the furnace combustion chamber significantly reduce heat transfer in the furnace, causing a decrease in overall efficiency of the furnace and the boiler. To avoid or reduce this effect, an intensive cleaning procedure is required. Most presently used cleaning procedures involve use-intensive air blowing, which is activated in a predetermined manner in different zones of the furnace and at a predefined periodicity. Numerous attempts have been made to optimize the process of air blowing, but all of them are based on theoretical models of heat transfer in the furnace and not on the direct measurement of the thickness of the growing deposit layer. Aside from this, no real data on the reflectivity of the deposits are available; reflectivity data can provide important information about the combustion conditions and total heat balance in the boiler. Keeping in mind that up to 95% of heat transfer in furnaces originates in the radiation component, strong skepticism exists with regard to modeling results which are not based on actual reflectivity/emissivity of the furnace wall.

In order to take fouling into account in the overall balance of the boiler, it is necessary to measure two main parameters—thickness of the deposits and their emissivity—in the wavelengths of visible and infrared (IR) region. The present inventors are aware of no patent or publication that suggests a system allowing direct measurement of fouling thickness and also of fouling reflectivity in real time, at a position inside an operating furnace. Several manufacturers have used heat flux sensors for indirect estimation of fouling thermal resistance, but this approach has substantial uncertainty, since heat flux is affected simultaneously by several parameters, including some in addition to fouling thickness. Apart from this, the installation of heat flux sensors is expensive and requires replacement of a part of the wall tube and therefore needs significant maintenance efforts.

The removal of fouling deposits by air jet is referred to as "soot blowing." Attempts to get better cleaning have led to improved efficiency of soot blowing; the use of sophisticated systems and cleaning procedures is called "intelligent soot blowing (ISB)." Existing ISB systems are based either on theoretical models of combustion and heat transfer inside the furnace or on calibration experiments. Since both approaches are predictive and not based on direct measurements, they cannot reflect variable dynamic conditions as they develop in the furnace, and therefore cannot be exploited for automatic soot blowing. To the best knowledge of the inventors, no automatic blowing system has been proposed up to now.

SUMMARY OF THE INVENTION

The invention provides an apparatus for real-time monitoring of the accumulation of fouling deposits inside a solid fuel firing furnace, as well as systems and methods using the apparatus. The apparatus optically determines the thickness of deposits as well as the reflectivity of the deposits at periodic intervals during the operation of the furnace. The apparatus can be integrated into an automated system for soot blowing to remove the deposits based on actual deposit formation data to achieve optimal performance and efficiency of the furnace.

One aspect of the invention is an apparatus for measuring the thickness of fouling deposits in a solid fuel firing furnace. The apparatus contains an optical probe, an illumination source, first and second optical paths, an imaging device, a standard specimen surface, a translocation mechanism, and a processor. The optical probe illuminates an inner surface of the furnace with illuminating light and receives a portion of the illuminating light as reflected light from the inner surface. The illuminating light is generated by the illumination source. The first optical path transmits the illuminating light through the optical probe and focuses it to form an illuminated spot on the inner surface of the furnace. The second optical path transmits the light reflected from the spot to the imaging device, which forms an image of the illuminated spot. The position of the spot in the image is determined by the thickness of the fouling deposits. Comparison of the spot image coordinates to known coordinates determined in the absence of the deposits, i.e., just after cleaning is finished, allows determination of the deposit thickness by the processor, which receives image data from the imaging device. The translocation mechanism is used to reversibly move the optical probe between an extended position in which the probe illuminates the inner surface of the furnace and a withdrawn position in which the probe illuminates the standard specimen surface within the apparatus. The translocation mechanism can be, for example, an electric motor or a mechanism driven by pressurized air. The standard specimen surface has a known reflectivity, and allows correction for any accumulation of deposits on the optical probe window, as well as determination of the absolute reflectivity of the inner surface of the furnace.

Another aspect of the invention is a system for automatic removal of fouling deposits in a solid fuel fired furnace. The system includes one or more fouling deposit measuring apparatuses as described above, one or more soot blowers, and a computer that receives output from the apparatuses and controls the soot blowers.

Still another aspect of the invention is a system for monitoring fouling deposits in a solid fuel fired furnace. The system includes one or more fouling deposit measuring apparatuses as described above and a computer that receives output from the apparatuses and analyzes fouling deposit levels in the furnace. In some embodiments, the computer also is associated with operation or control of the furnace.

Yet another aspect of the invention is a method of analyzing fouling deposits in a solid fuel fired furnace in real time. The method includes the following steps: (a) providing an apparatus as described above, which is installed on a solid fuel fired furnace; (b) moving the optical probe of the apparatus from the withdrawn to the extended position, whereby the optical probe enters the furnace; (c) illuminating an inner surface of the furnace using the optical probe to form a focused illuminating spot on the inner surface; (d) recording a first image using reflected light from the inner surface; (e) moving the optical probe from the extended to the withdrawn position; and (f) determining a thickness of fouling deposits on the inner surface from a change in position of the spot between the first image and a corresponding image recorded when the inner surface was free of fouling deposits. In certain embodiments, the method further determines the absolute reflectivity of the inner surface of the furnace by including the following additional steps performed after step (e): (e1) illuminating the standard specimen surface of the apparatus using the optical probe in the withdrawn position to form a focused illuminating spot on the standard surface, the standard surface having a known absolute reflectivity; (e2) recording a second image using reflected light from the standard surface; and (e3) determining absolute reflectivity of the inner surface by comparing spot intensities in the first image and the second image of the furnace by dividing the spot intensities in the first image by those in the second image and multiplying the result by the absolute reflectivity of the standard surface.

DETAILED DESCRIPTION OF THE INVENTION

Figure 1A:
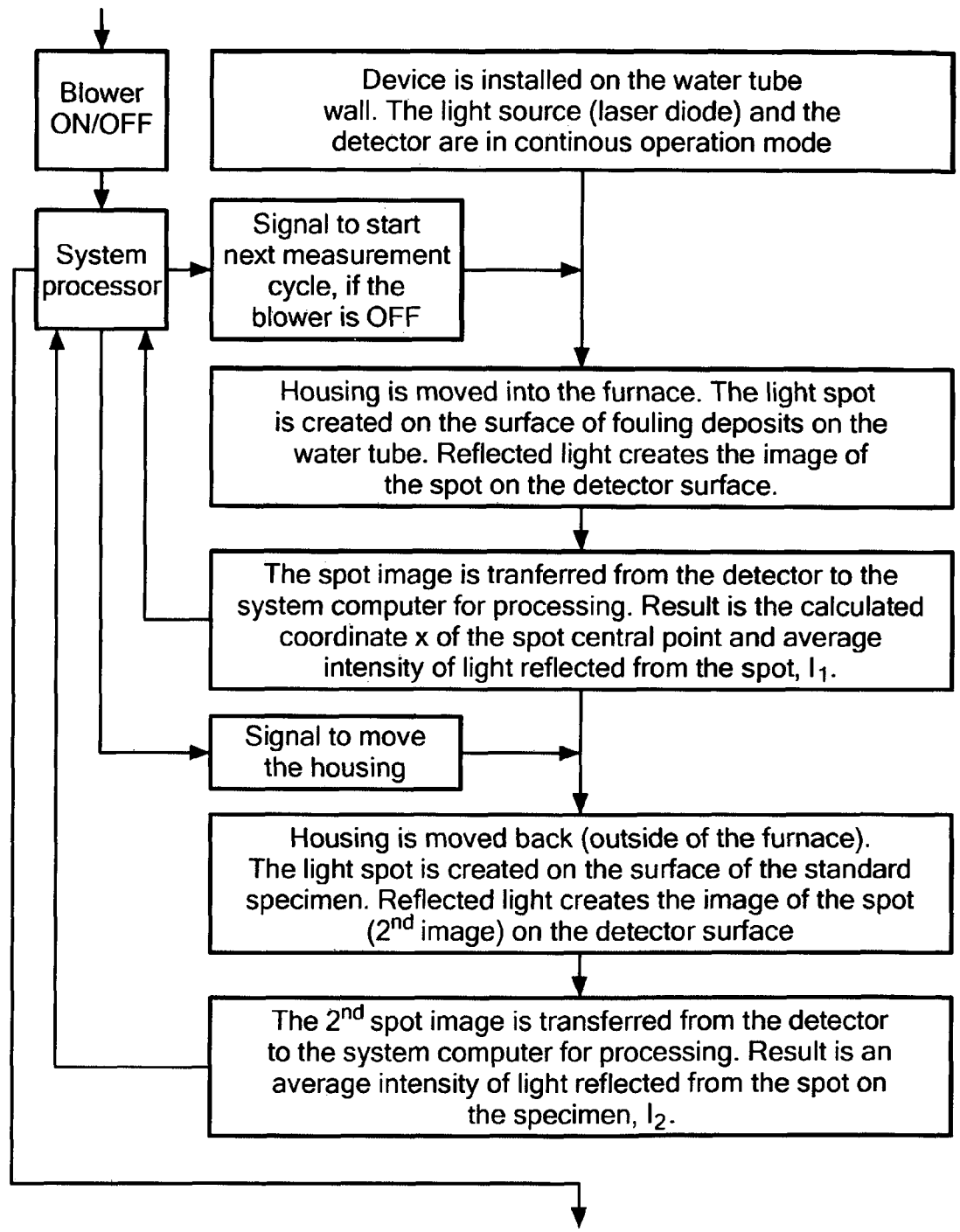
FIGS. 1A and 1B present a flow chart of a method for automatic soot blowing according to the invention.

The present inventors have developed an apparatus that makes possible the real time monitoring of fouling deposits within a solid fuel firing furnace, such as a pulverized coal furnace. The apparatus uses optical methods to determine the thickness and/or reflectivity of the deposits at selected intervals while the furnace is operating. Use of the apparatus requires no changes to the normal operation of the furnace. The apparatus is mounted on the outside of the combustion chamber of the furnace, and includes an optical probe that extends into the combustion chamber through a hole in the combustion chamber wall, takes optical measurements from an interior surface of the combustion chamber, such as the surface of water tubes within the wall of the combustion chamber, and then withdraws from the combustion chamber to an externally mounted housing. Preferably, the optical probe closes off the hole in the combustion chamber wall when in the withdrawn position. The optical probe is designed for use within the harsh conditions of the combustion chamber. The apparatus is preferably adapted for measuring the thickness of fouling deposits on the water tubes of an inner wall of a furnace, in that the apparatus is installed on a portion where its optical probe can enter through the wall near such water tubes and its optical probe has one or more windows and other optical elements aligned so that deposits on the nearby water tubes can be illuminated and reflected light from the tubes can be collected. The apparatus can be used to regulate a soot blower and to form an automated soot blowing system to remove the deposits based on actual deposit formation data to achieve optimal performance and efficiency of the furnace.

The apparatus uses a method that is based on the illumination of a spot on an inner surface of a furnace subject to the accumulation of fouling deposits. Light that is reflected off the deposits at the illuminated spot is collected by the optical probe of the apparatus, and the reflected light is projected onto an imaging detector within the apparatus. The illumination light path (first optical path) and imaging light path (second optical path) are configured in such a way that a change of position of the deposit surface, due to increased deposit thickness, results in a change of position of the spot image at the imaging detector. By comparing the spot image location to a calibration, the actual deposit thickness can be calculated. In a preferred embodiment, the apparatus is calibrated in a laboratory as follows: (1) a light spot created by the first optical path is directed onto a flat calibration surface; (2) light reflected from the flat calibration surface is transmitted by the second optical path to form a first spot image on the imaging device; (3) the flat calibration surface is moved by a precisely known first length to mimic the accumulation of deposits of a known thickness, and steps (1) and (2) are repeated, resulting in a second spot image, whose position differs from the position of the first spot image by a precisely known second length; (4) a calibration factor is determined from the first length and the second length. During an actual measurement under furnace operating conditions, the deposit thickness accumulated between two measurements can be obtained by multiplying the calibration factor times the difference in spot positions (i.e., shift in image position coordinates) between the two measurements. In addition, by measuring the intensity of light incident on the deposit and the intensity of light reflected back from the deposit, the reflectivity of the deposit surface can be calculated, which provides further information to the furnace operator. That is, the intensity of light, $I_D$, reflected from the deposit is measured, as well as the intensity of light, $I_S$, reflected from the standard surface with known reflectivity, $R_S$. The reflectivity of the deposit, $R_D$, can then be calculated as $R_D = (I_D/I_S) \times R_S$.

An apparatus of the invention can be combined into a variety of possible systems. One such system includes two or more apparatuses of the invention that are installed in different locations in a single furnace. For example, up to 5, 10, 15, 20 or more apparatuses of the present invention can be used on a single furnace. The results obtained from the apparatuses installed on a single furnace can be fed to a single processor or computer for analysis of heat transfer in different zones of the furnace. Alternatively, the output of the apparatuses can be displayed in a control room where the operation of the furnace is regulated. Another system includes one or more, or two or more, apparatuses of the invention whose output is sent to a processor or computer that in turn controls the operation of one or more soot blowers within the same furnace.

Figure 1B:
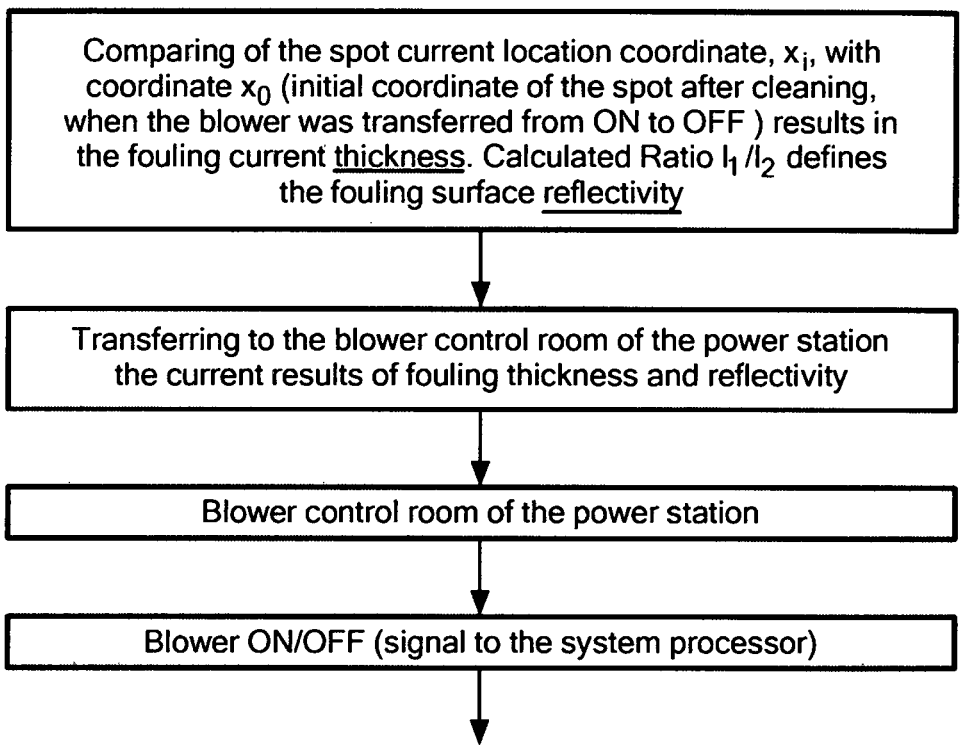

Using the present invention, measurement results can be transferred in real time to the control room of a power station, from which soot blowers are either activated or shut down. When the growing thickness of deposits achieves a predefined value, the blower near the point of measurement is activated, and creates an air jet (or in some embodiments a water stream or jet) that cleans the water tube wall inside the furnace. At the beginning of a blower activation cycle, a signal is transferred to the processing unit of the apparatus, which stops the measuring cycle and prevents possible damage to the apparatus. After several minutes, at the end of the cleaning cycle, the blower is commanded to cease operation, and another signal is transferred from the control room to the processing unit of the apparatus. In response, the position of the reflected light spot on the imaging device is again measured, and the position is set to correspond to zero measured thickness. A new measurement cycle then begins. Using this method, soot blowers can be automatically activated when cleaning is really needed, instead of being activated according to an artificially predefined program. The flow chart shown in FIG. 1 illustrates an embodiment of this process.

Figure 2:
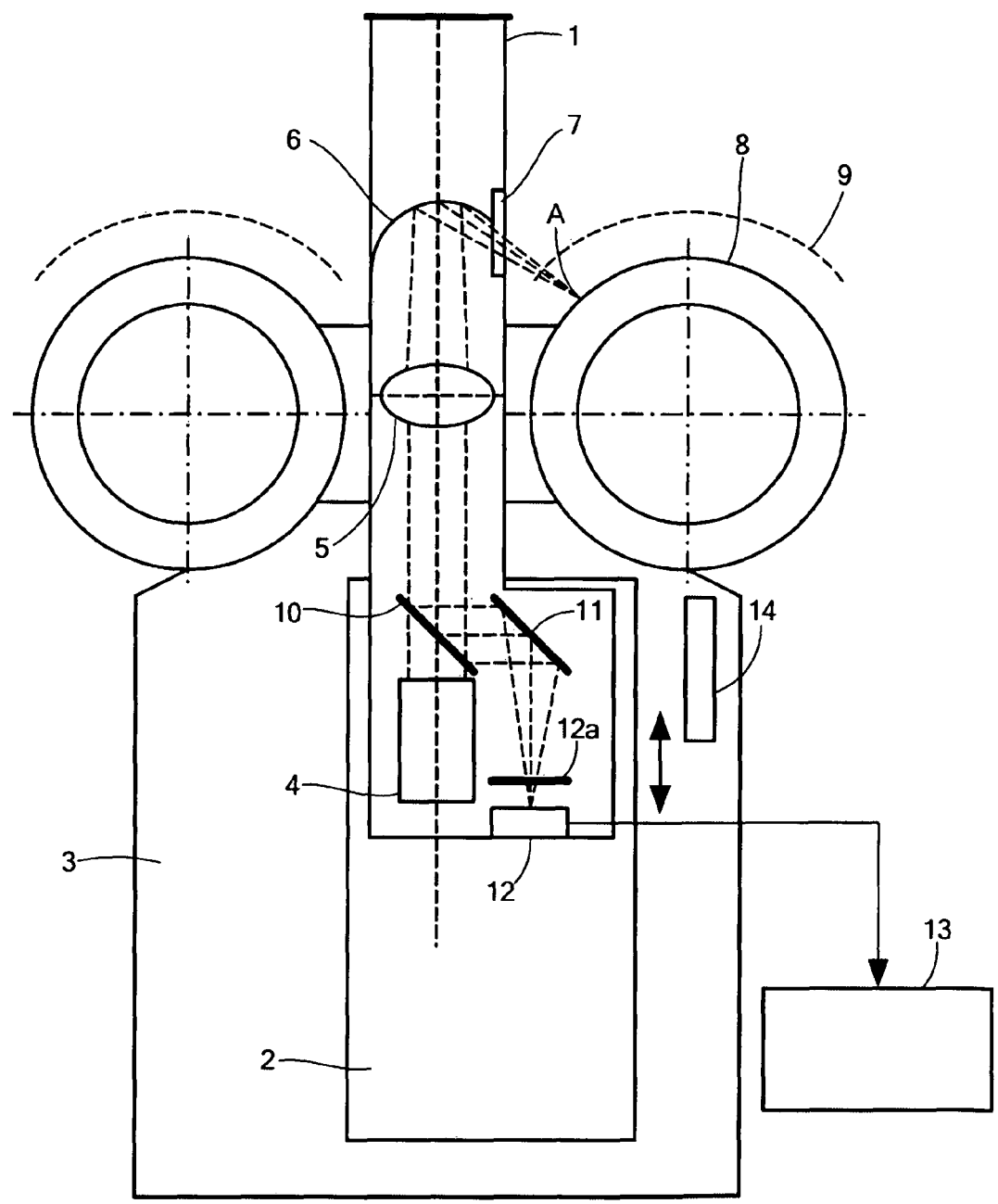
FIG. 2 shows a schematic cross-sectional view of an embodiment of an apparatus for detecting fouling deposits in a solid fuel fired furnace. During operation, the optical probe portion is pushed forward inside the furnace combustion chamber as depicted (extended position).
Figure 3:
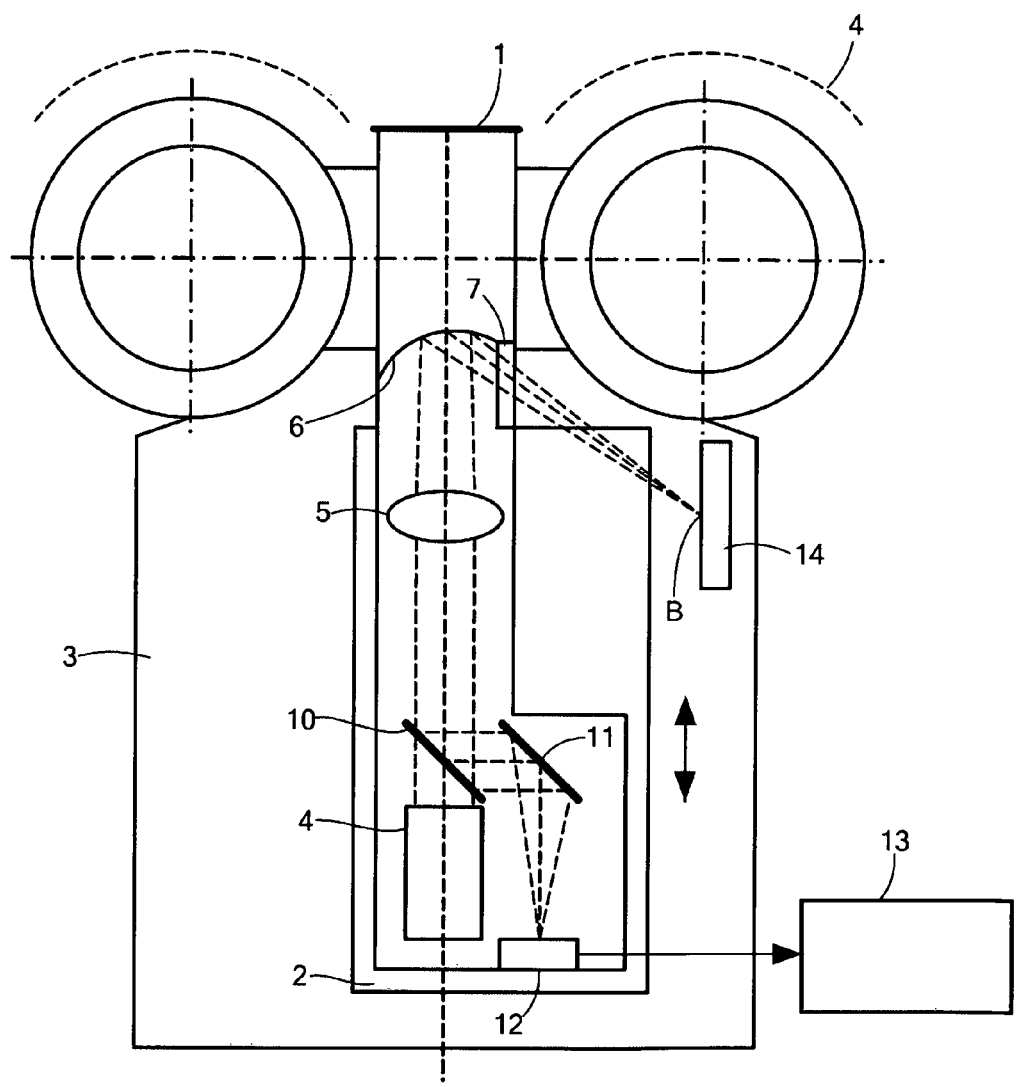
FIG. 3 shows a schematic cross-sectional view of the same embodiment shown in FIG. 2, but with the optical probe pulled back and positioned outside of the combustion chamber (withdrawn position).
Figure 4:
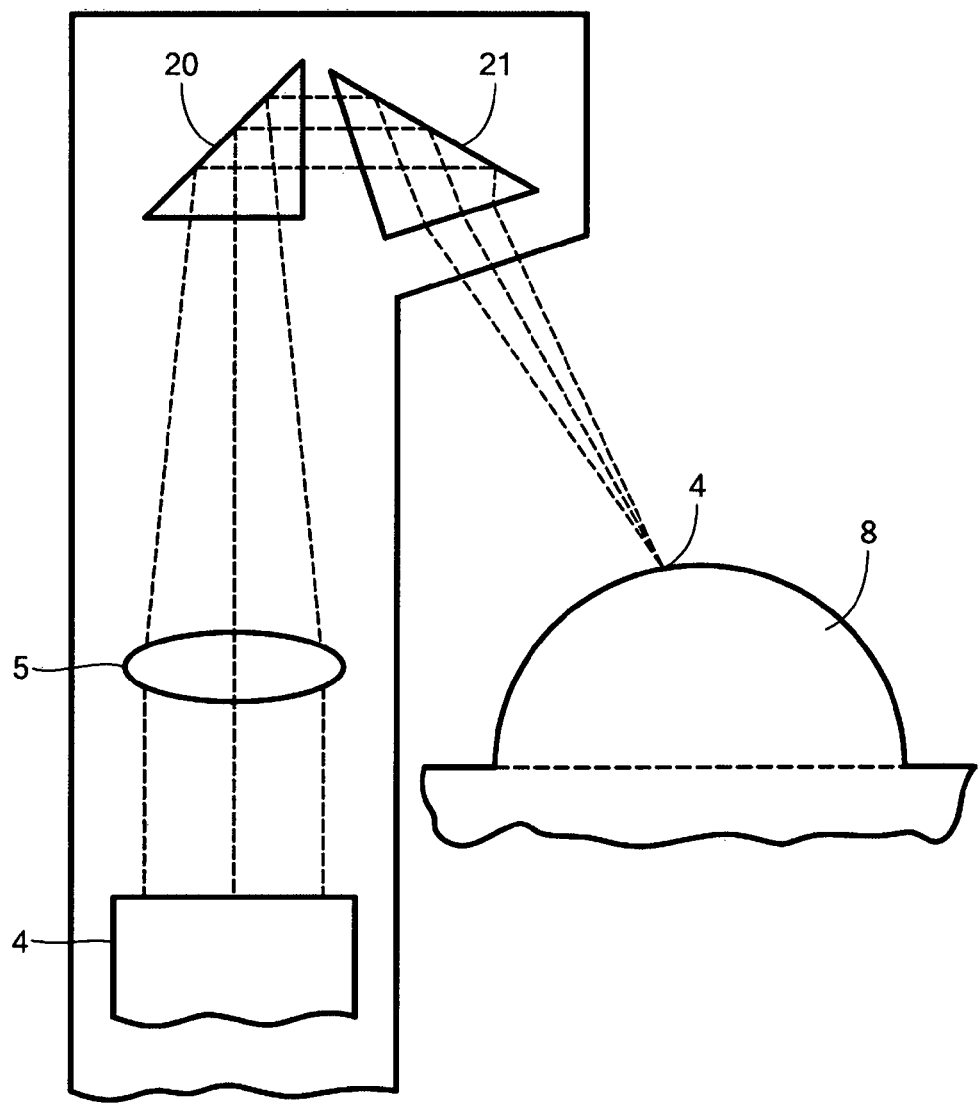
FIG. 4 shows a schematic cross-sectional view of an embodiment of the optical probe portion of an apparatus for detecting fouling deposits in a solid fuel fired furnace. In this embodiment, an arrangement of prisms forms part of the optical pathway used in the high temperature environment of the furnace.

The present method can be implemented in an electro-optical apparatus such as that further described below and depicted schematically in FIGS. 2-4. Referring now to FIG. 2, optical components of the apparatus are located in optical probe 1 which moves on slide 2 positioned in housing 3. The housing is connected to the walls of a furnace, but is located outside of the firing chamber where the fuel is burnt. Movement of optical probe 1 into and out of the furnace enables the illumination of either point A on the tube wall (i.e., with the optical probe in the extended position) or point B on standard specimen 14 (i.e., with the optical probe in the withdrawn position). Movement of the optical probe back into the furnace for another measurement is carried out periodically, at a rate compatible with the rate of generation of fouling deposits.

The apparatus depicted in FIG. 2 includes monochromatic light source 4. The light source can be a laser diode or LED or any other suitable monochromatic light source. The light source produces light in the visible and/or infrared range, preferably in the range from 0.6 to 3 microns in wavelength. The light beam originating from the light source is focused by lens 5 and concave mirror 6 onto the surface of the fouling deposits on tube wall 8. When the tube is clean, the focused light spot is created at point A. On the other hand, when deposits are present, the illuminated spot moves to a new point determined by deposit surface 9. A portion of the light scattered (reflected) by surface 9 is collected by the optics of the apparatus and is directed by beam splitter 10 and mirror 11 onto imaging detector 12. The imaging detector can be, for example, a CCD camera or any other image position sensor, and it is interfaced to processing unit 13. Image data from the imaging detector are transferred to the processing unit for analysis, including determination of the spot position coordinates. The spot image position can be represented, for example, by coordinates of a median, calculated according to a known standard algorithm operated on the 2D array of light intensity inside the spot image, or by any other representative point of the spot image.

Detector 12 is covered by a narrow band pass filter 12a which allows the wavelength emitted by monochromatic light source 4 to pass while filtering out other wavelengths. Standard commercially available interference filters configured as band pass filters having Full Width at Half Maximum (FWHM) of 7-10 nm can be used for this purpose. Such a band pass filter has a high transmission for the specific wavelength of illumination and strongly blocks radiation of other wavelengths existing in the furnace environment and reflected by the fouling deposit surface in a diffusive manner, i.e., in all directions including in the direction of window 7. In such a way electromagnetic radiation reaching detector 12 mainly originates from the light source of the apparatus and not from the intense thermal radiation present in the furnace.

During typical operation of a pulverized coal-fired furnace, fouling can be deposited not only on the wall tubes, but also on the surface of window 7 of the apparatus of the invention. As a result, transparency of the window may decrease significantly during operation, which causes a bias of the detector reading and leads to errors in reflectivity measurements. To avoid such errors, window 7 preferably remains in the optical path of the light beam when the standard specimen is illuminated (see FIG. 3), and reflected light is measured from the standard each time reflected light is measured from fouling deposits. In this way, the change of window transparency influences both measured values to the same extent and therefore does not affect the relative reflectivity. Preferably, the apparatus window can be cleaned during planned periodic maintenance of the furnace.

Furthermore, the surface of the fouling deposits and the surface of the specimen are diffusive and therefore scatter the reflected light in all direction, not only in the direction of the window 7. The absolute reflectivity of each of two surfaces depends on the angle of incidence and the angle of light collection. Due to the geometry of the suggested arrangement, the direction of the incident beam and that of the collected beam remain the same in both positions of optical probe 1, when reflection of the deposit and reflection of the specimen are measured. However, the angle of incidence is different in these two measurements because the orientation of the tube surface and the orientation of specimen surface with regard to the incident beam are different. To take this into account, the absolute reflectivity of specimen 14 is measured in advance, under laboratory conditions, and at the correct angular position dictated by the geometry of the arrangement optics. This absolute reflectivity value for the standard specimen is used when the system processor calculates the reflectivity of the fouling deposits.

For better separation of radiation originating in the measurement apparatus from thermal radiation existing in the furnace, light source 4 can be modulated. For example, the light source can be modulated by an alternating current (AC) at a selected frequency, such as a frequency in the range from about 1 kHz to about 10 kHz. The same frequency should be detected at the output of detector 12, and its AC intensity can be measured in the reflected radiation, thereby reducing or eliminating the signal from extraneous radiation reaching the detector.

The apparatus of the invention is intended to be operated within the high temperature environment of an operating furnace. Therefore, the optical probe and its internal components preferably should have no optical coatings or adhesive materials that could degrade in such an environment. In order to accomplish this, a configuration of optical components based on total internal reflection, and lacking upper mirrors such as mirror 6 in FIGS. 2 and 3, can be used. An embodiment having an architecture that uses total reflection is shown in FIG. 4. In this embodiment, prisms 20 and 21, which can be made of fused silica or ruby, for example, are used to capture incident radiation and direct it into the optical path towards the image detector. A similar configuration of prisms can be exploited in the optical path of reflected light within the apparatus, below the optical probe.

A soot deposit measuring apparatus of the present invention can be used to carry out several methods associated with analysis of deposits in an operational solid fuel fired furnace and/or controlling the operation of such a furnace. One such method analyzes fouling deposits in a solid fuel fired furnace in real time. An apparatus according to the invention is installed on a solid fuel fired furnace, so that its optical probe can move in and out through a side wall of the furnace, between withdrawn and extended positions. When the optical probe enters the furnace, it illuminates an inner surface (e.g., the inner surface of the wall penetrated by the optical probe) and forms a focused illuminating spot on the inner surface. A first image of the illuminated spot is then recorded using reflected light from the inner surface. The optical probe is then moved from the extended position to the withdrawn position. The thickness of fouling deposits on the inner surface is then determined (i.e., calculated) from a change in position of the spot between the first image and a corresponding image recorded when the inner surface was free of fouling deposits, such as just after the last cleaning cycle using soot blowers, or after periodic maintenance and cleaning of the furnace. Optionally, the method can be repeated at selected time intervals during the operation of the furnace, whereupon the accumulation of deposits is monitored over time.

In some embodiments of the method of measuring or analyzing soot deposits, a cleaning cycle is activated to remove fouling deposits within the furnace using a soot blower upon reaching a preselected deposit thickness or distribution within the furnace. For example, data can be obtained from two or more apparatuses installed on the same furnace, and the data can be analyzed to determine when and/or where a cleaning cycle within the furnace is activated and soot blowers are turned on and off. The apparatus can itself turn soot blowers on and off based on measured deposit thickness, or data provided by the apparatus to a computer can be used to activate a soot blower cleaning cycle using the computer. After a cleaning cycle has been completed, it is preferred that the apparatus immediately take a new measurement (i.e., obtain an image of the inner wall) to serve as a baseline for comparison to later measurements, and to set a "zero" or baseline thickness level (i.e., spot image position in the imaging device) used to calculate deposit thickness at later times and as soot deposits build up on the inner wall.

As the apparatus of the current invention can be readily installed on a furnace that operates in an electrical power generating station, the apparatus processor and/or its data output can be connected to a soot blower control room or other control center of the power station. The use of the apparatus is preferred for power station furnaces fired by pulverized coal. An advantage of the apparatus is that its operation can be carried out while the furnace is operating and burning fuel and when the power station is on line.

In some embodiments of the method of analyzing deposits within a furnace using an apparatus of the invention, the method includes additional steps to determine the reflectivity of an inner surface of the furnace. In order to measure the reflectivity, a standard specimen surface within the apparatus is illuminated using the optical probe in the withdrawn position. A focused illuminating spot is formed on the standard surface, which has a known absolute reflectivity. A second image is recorded using reflected light from the standard surface. The intensity of light in the second image is compared to the intensity of light in the earlier determined first image of the inner wall of the furnace. By comparison of the intensities from the first and second images, the absolute reflectivity of the inner surface is determined.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. An apparatus for measuring the thickness of fouling deposits in a solid fuel firing furnace, the apparatus comprising:
    an optical probe that illuminates an inner surface of the furnace with illuminating light and receives a portion of the illuminating light as reflected light from the inner surface;
    an illumination source that generates the illuminating light;
    a first optical path that transmits the illuminating light through the optical probe and focuses it to form an illuminated spot on the inner surface;
    an imaging device;
    a second optical path that transmits the reflected light through the optical probe to the imaging device, the imaging device forming an image of the illuminated spot, wherein the position of the spot in the image is determined by the thickness of the fouling deposits;
    a standard specimen surface having a known reflectivity;
    a translocation mechanism for reversibly moving the optical probe between an extended position in which the probe illuminates the inner surface of the furnace and a withdrawn position in which the probe illuminates the standard specimen surface; and
    a processor that receives image data from the imaging device and determines the thickness of the fouling deposits based on the position of the spot in the image.

2. The apparatus of claim 1, wherein the optical probe comprises a window through which said illuminating light and said reflected light are transmitted.

3. The apparatus of claim 1, wherein the imaging device is a CCD camera or an array of photodiodes.

4. The apparatus of claim 1, wherein the illumination source outputs monochromatic light.

5. The apparatus of claim 4, wherein the illumination source is a laser diode.

6. The apparatus of claim 5, wherein the laser diode is driven by an alternating current.

7. The apparatus of claim 6, wherein the alternating current has a frequency in the range from about 1 kHz to about 10 kHz.

8. The apparatus of claim 1, wherein the illuminating light has a wavelength in the range from about 0.6 μm to about 3 μm.

9. The apparatus of claim 1, wherein the optical probe in the extended position is at least partially disposed within a combustion chamber of the furnace, and the illumination source, imaging device, standard specimen, and processor are disposed outside the combustion chamber.

10. The apparatus of claim 9, wherein the optical probe in the withdrawn position is disposed at least partially outside the combustion chamber.

11. The apparatus of claim 1, wherein the illumination source, imaging device, standard specimen, and processor are disposed within a housing mounted on an outer surface of the furnace.

12. The apparatus of claim 11, wherein the housing is mounted outside a combustion chamber of the furnace and the optical probe travels into and out of the combustion chamber through a hole in a wall of the combustion chamber as it moves between said extended position and said withdrawn position.

13. The apparatus of claim 12, wherein an upper surface of the optical probe closes the hole in the combustion chamber wall when the optical probe is in the withdrawn position.

14. The apparatus of claim 1, wherein the translocation mechanism is driven by an electric motor or pressurized air.

15. The apparatus of claim 1, wherein said one or more optical elements are disposed (i) within the optical probe or (ii) outside the optical probe but within a housing mounted on an outer surface of the furnace, or both.

16. The apparatus of claim 1 comprising one or more optical elements that are free of optical coatings and/or adhesives.

17. The apparatus of claim 1 comprising one or more optical elements having total internal reflection.

18. The apparatus of claim 1, wherein the illuminating light is monochromatic.

19. The apparatus of claim 18, further comprising a bandpass filter that transmits the wavelength of the monochromatic illuminating light, the filter mounted in the second optical path prior to the imaging device.

20. The apparatus of claim 1 that measures reflectivity of the inner surface.

21. The apparatus of claim 20, wherein absolute reflectivity is determined from an intensity of light reflected from the inner surface, an intensity of light reflected from the standard specimen surface, and the absolute reflectivity of the standard specimen surface.

22. The apparatus of claim 1, wherein the solid fuel is pulverized coal.

23. The apparatus of claim 1 that automatically activates and deactivates a soot blower within the furnace based on measured thickness of the fouling deposits.

24. The apparatus of claim 1 that measures the thickness of the fouling deposits in real time while the furnace is fired.

25. The apparatus of claim 1 that measures the reflectivity of the fouling deposits in real time while the furnace is fired.

26. The apparatus of claim 1 that measures both the thickness and reflectivity of the fouling deposits in real time while the furnace is fired.

27. The apparatus of claim 1 adapted for measuring the thickness of fouling deposits on an inner wall containing water tubes.

28. The apparatus of claim 27, wherein thickness of fouling deposits on the water tubes is measured.

29. The apparatus of claim 1 that is pre-calibrated using a reflective surface at two controlled locations representing a known thickness of fouling deposits, and the known thickness is correlated with a shift in position coordinates of images of an illuminated spot recorded on the imaging device, the images corresponding to said controlled locations.

30. A system for automatic removal of fouling deposits in a solid fuel fired furnace, the system comprising:
one or more fouling deposit measuring apparatuses of claim 1;
one or more soot blowers; and
a computer that receives output from the apparatuses and controls the soot blowers.

31. The system of claim 30, wherein the computer is associated with control of the furnace.

32. A system for monitoring fouling deposits in a solid fuel fired furnace, the system comprising:
one or more fouling deposit measuring apparatuses of claim 1; and
a computer that receives output from the apparatuses and analyzes fouling deposit levels in the furnace.

33. A method of analyzing fouling deposits in a solid fuel fired furnace in real time, the method comprising the steps of:
(a) providing the apparatus of claim 1 which is installed on a solid fuel fired furnace;
(b) moving the optical probe of the apparatus from the withdrawn to the extended position, whereby the optical probe enters the furnace;
(c) illuminating an inner surface of the furnace using the optical probe to form a focused illuminating spot on the inner surface;
(d) recording a first image using reflected light from the inner surface;
(e) moving the optical probe from the extended to the withdrawn position; and
(f) determining a thickness of fouling deposits on the inner surface from a change in position of the spot between the first image and a corresponding image recorded when the inner surface was free of fouling deposits.

34. The method of claim 33, further comprising repeating steps (b) through (i) at selected time intervals during the operation of the furnace.

35. The method of claim 33, further comprising:
(g) activating a cleaning cycle to remove fouling deposits within the furnace using a soot blower.

36. The method of claim 35, wherein data obtained from two or more apparatuses of claim 1 installed on the same furnace are analyzed to determine when and/or where a cleaning cycle within the furnace is activated and soot blowers are turned on and off.

37. The method of claim 35, wherein the soot blower is turned on and off.

38. The method of claim 35, wherein a new measurement cycle comprising steps (b) through (f) is started after the soot blower is turned off in order to establish a new baseline for a subsequent cycle of analyzing fouling deposits.

39. The method of claim 35, wherein the furnace operates in a power generating station.

40. The method of claim 39, wherein fouling deposit thickness and/or inner surface reflectivity data are transmitted to a soot blower control room of the power station.

41. The method of claim 33, wherein the furnace is fired by pulverized coal.

42. The method of claim 33, wherein steps (b) through (f) are performed while the furnace is operating and burning fuel.

43. The method of claim 33, wherein the method further comprises the steps of:
(e1) illuminating the standard specimen surface of the apparatus using the optical probe in the withdrawn position to form a focused illuminating spot on the standard surface, the standard surface having a known absolute reflectivity;
(e2) recording a second image using reflected light from the standard surface; and
(e3) determining absolute reflectivity of the inner surface by comparing spot intensities in the first image and the second image.

* * * * *